United States Patent [19]

Yehl et al.

[11] Patent Number: 5,010,777

[45] Date of Patent: * Apr. 30, 1991

[54] APPARATUS AND METHOD FOR ESTABLISHING SELECTED ENVIRONMENTAL CHARACTERISTICS

[75] Inventors: James E. Yehl; Rex R. Coppom, both of Boulder, Colo.

[73] Assignee: American Environmental Systems, Inc., Boulder, Colo.

[ * ] Notice: The portion of the term of this patent subsequent to Mar. 27, 2007 has been disclaimed.

[21] Appl. No.: 365,670

[22] Filed: Jun. 13, 1989

Related U.S. Application Data

[63] Continuation-in-part of Ser. No. 138,143, Dec. 28, 1987, Pat. No. 4,911,737, and a continuation-in-part of Ser. No. 300,121, Jan. 23, 1989.

[51] Int. Cl.$^5$ .............................................. G01N 1/12
[52] U.S. Cl. ..................................... 73/864.81; 55/12; 55/131; 55/139; 55/126; 55/385.2; 55/154; 361/231; 98/31.5
[58] Field of Search .................. 55/2, 12, 124, 126, 55/131, 136–138, 139, 154, 385.2; 98/31.5, 33, 115.3; 361/230–235; 73/864.81

[56] References Cited

U.S. PATENT DOCUMENTS

| Re. 27,027 | 1/1972 | Cristofv et al. | 128/190 |
|---|---|---|---|
| 2,184,644 | 12/1939 | Homberger | 128/371 |
| 2,264,495 | 12/1941 | Wilner | 361/235 |
| 2,650,672 | 9/1953 | Barr et al. | 55/139 |
| 3,678,337 | 7/1972 | Grauvogel | 317/4 |
| 3,680,281 | 8/1972 | Jahnke et al. | 55/106 |
| 3,711,743 | 1/1973 | Bolasny | 317/3 |
| 3,973,927 | 8/1976 | Furchner | 55/139 |
| 4,530,272 | 7/1985 | Stokes | 55/385.2 |
| 4,699,640 | 10/1987 | Suzuki et al. | 55/385.2 |
| 4,757,421 | 7/1988 | Mykkanen | 361/235 |
| 4,811,159 | 3/1989 | Foster | 361/231 |

FOREIGN PATENT DOCUMENTS

| 3201835 | 6/1983 | Fed. Rep. of Germany | 55/131 |
|---|---|---|---|
| 3528590 | 2/1987 | Fed. Rep. of Germany | 55/385.2 |

*Primary Examiner*—Bernard Nozick
*Attorney, Agent, or Firm*—Harold A. Burdick

[57] ABSTRACT

An apparatus and method for establishing selected environmental characteristics in a substantially enclosed area is disclosed for removal of undesired matter therefrom while establishing selected predetermined desired environmental characteristics therein. The apparatus includes structure establishing the substantially enclosed area, the structure having units for negative ion production and positive electrostatic field establishment positioned therein. The electrostatic field establishing unit includes a field collector and pulse generating circuitry for pulsating the positive electrostatic field at a selected frequency, the field collector preferably having a collector surface which is removable and subject to processing to enable analysis of matter collected thereat. The apparatus includes controls for selectively controlling ion output, field strength, field pulsation frequency and selected functions of a fluid directing and conditioning system, and may include full spectrum lighting, structural and/or occupant grounding and/or a supplemental source of free oxygen.

25 Claims, 9 Drawing Sheets

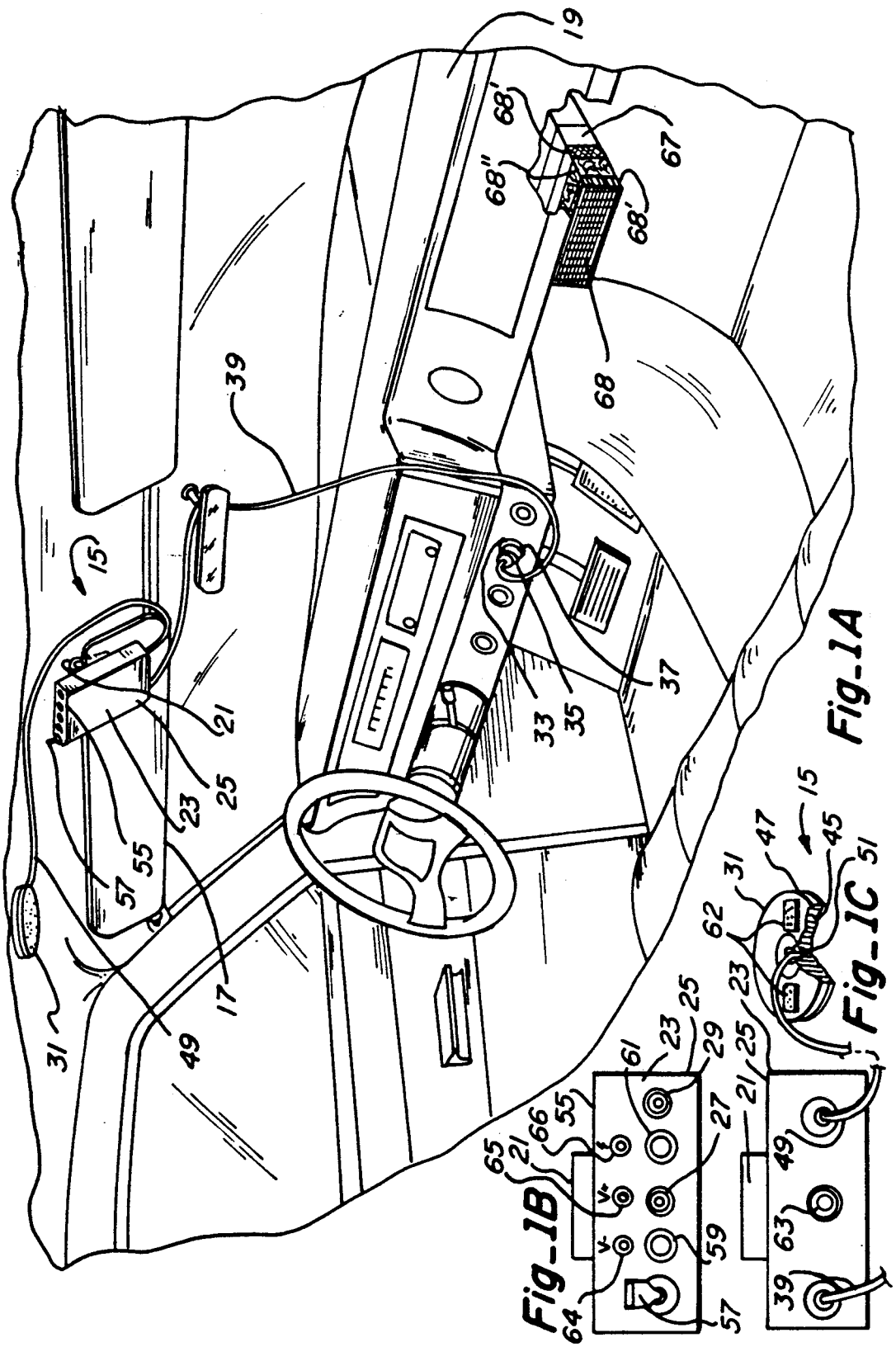

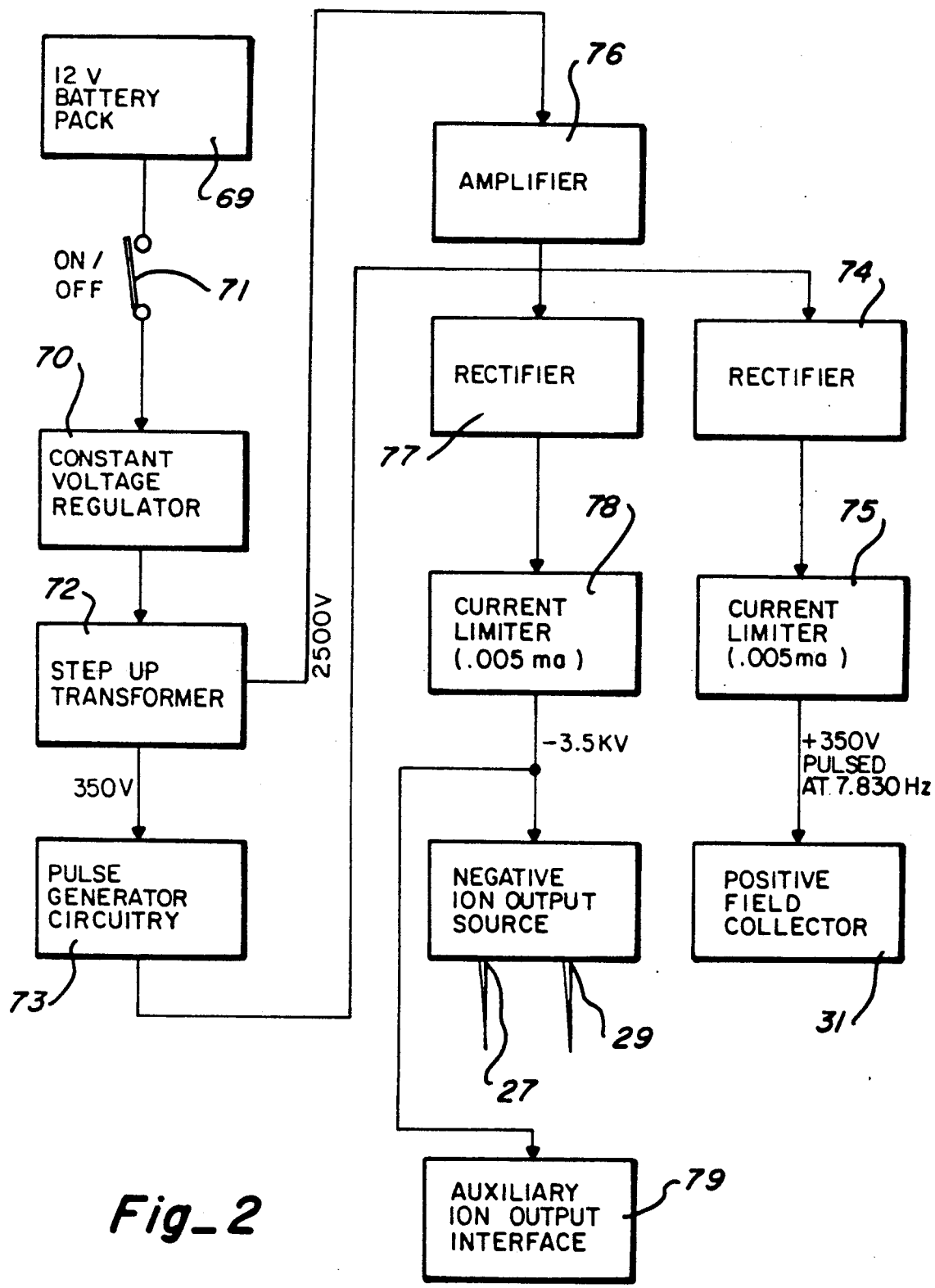
Fig_2

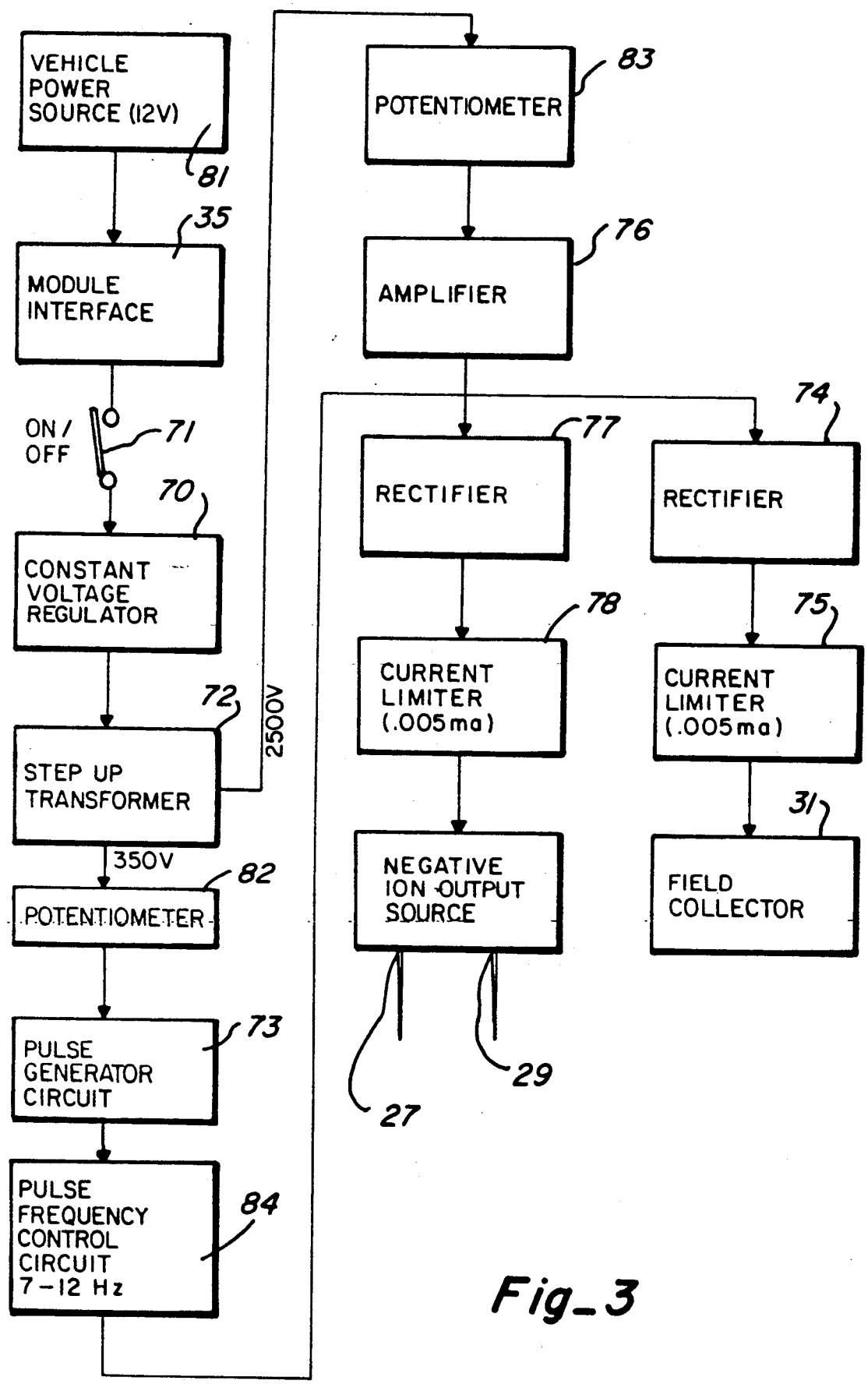
Fig_3

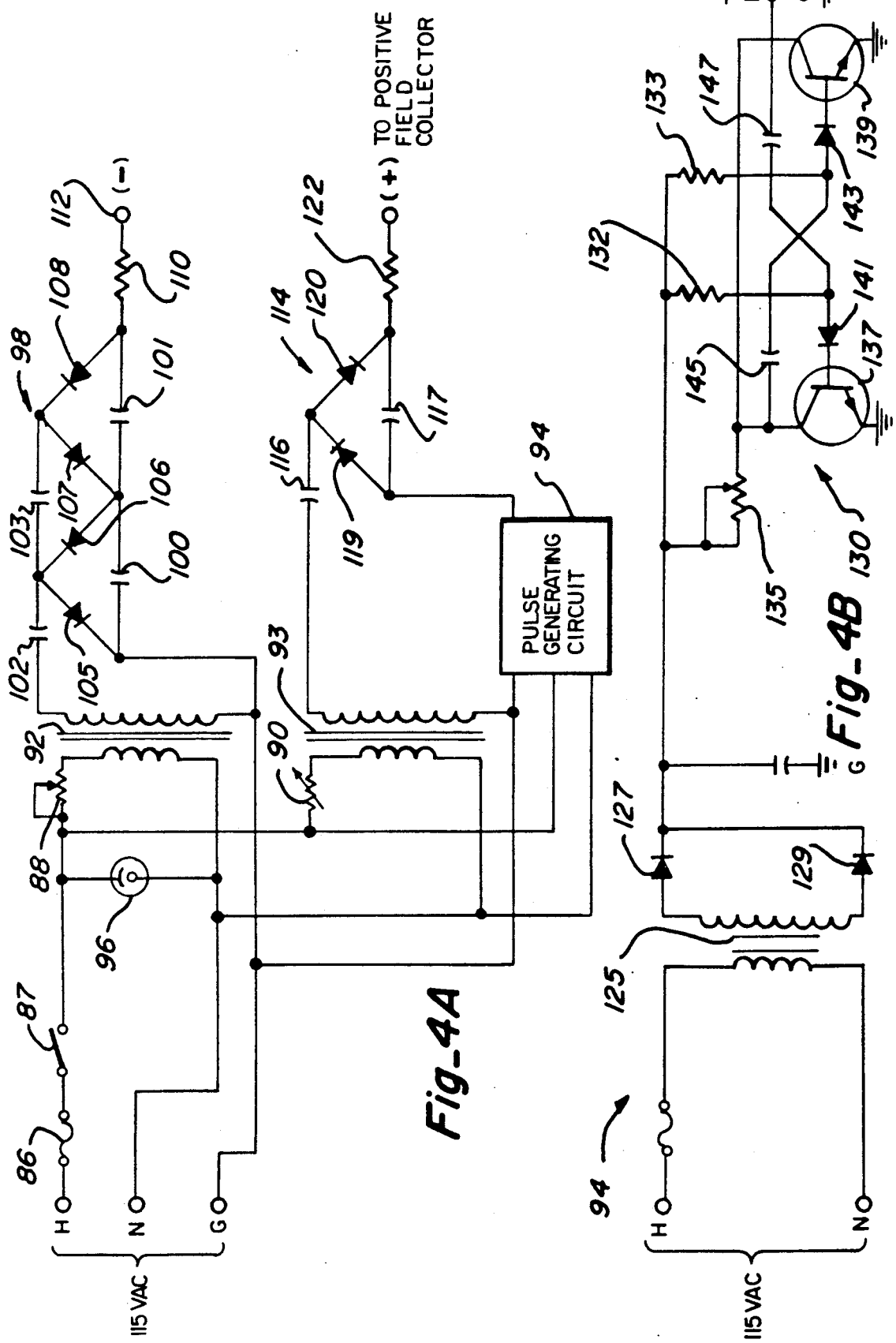

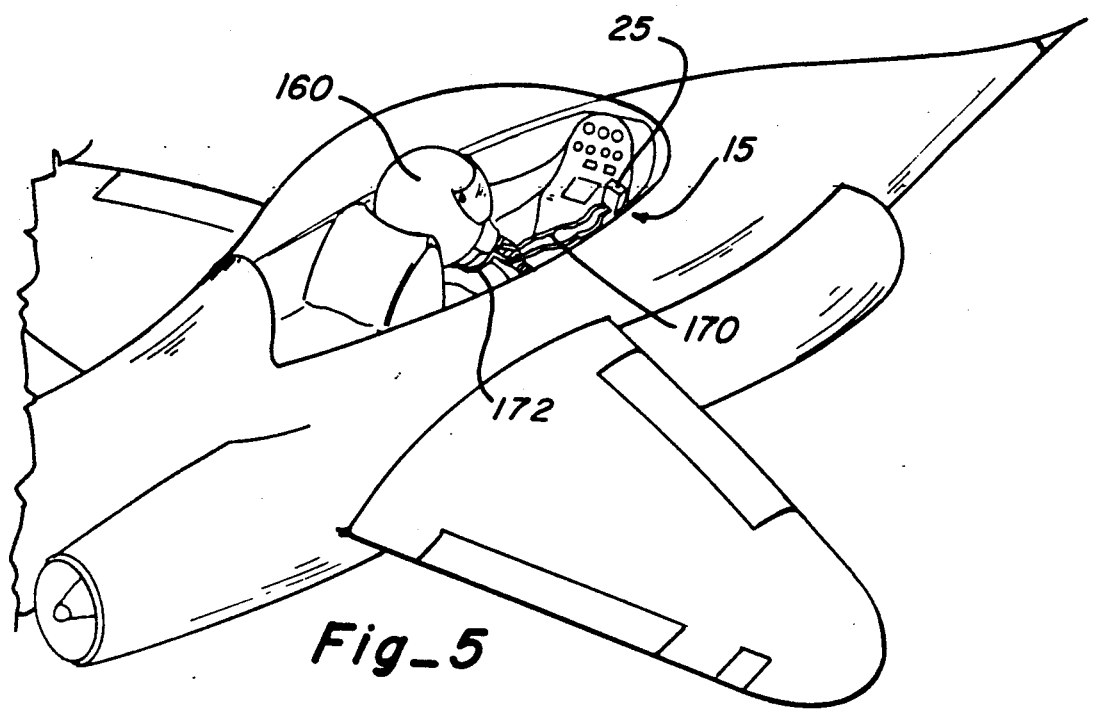
Fig_5
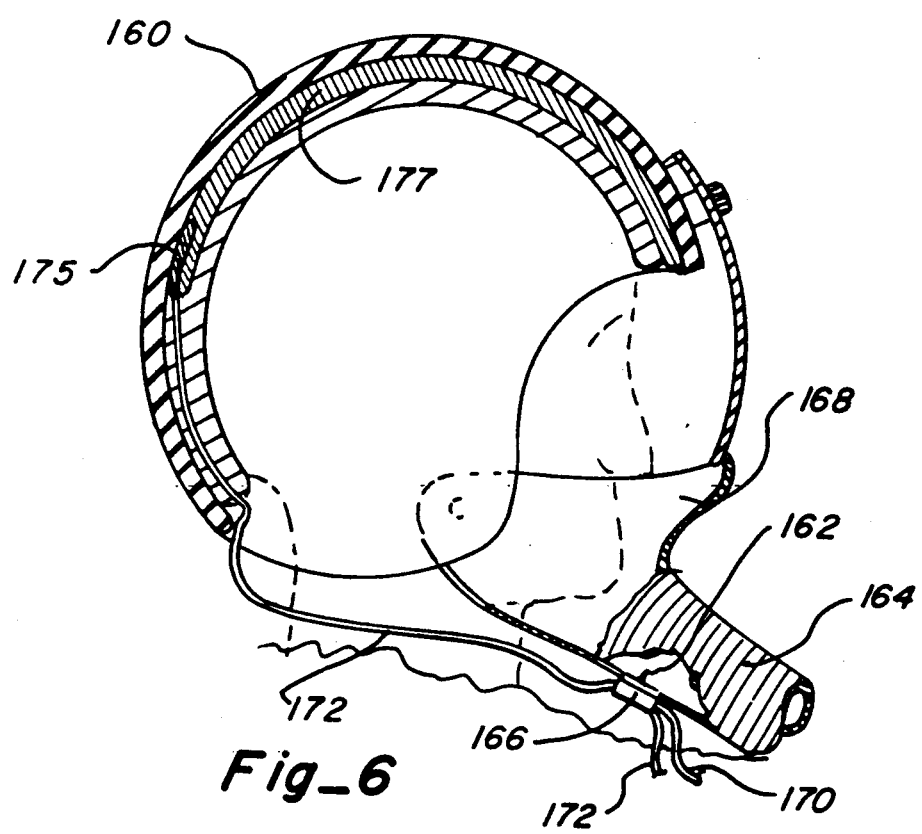
Fig_6

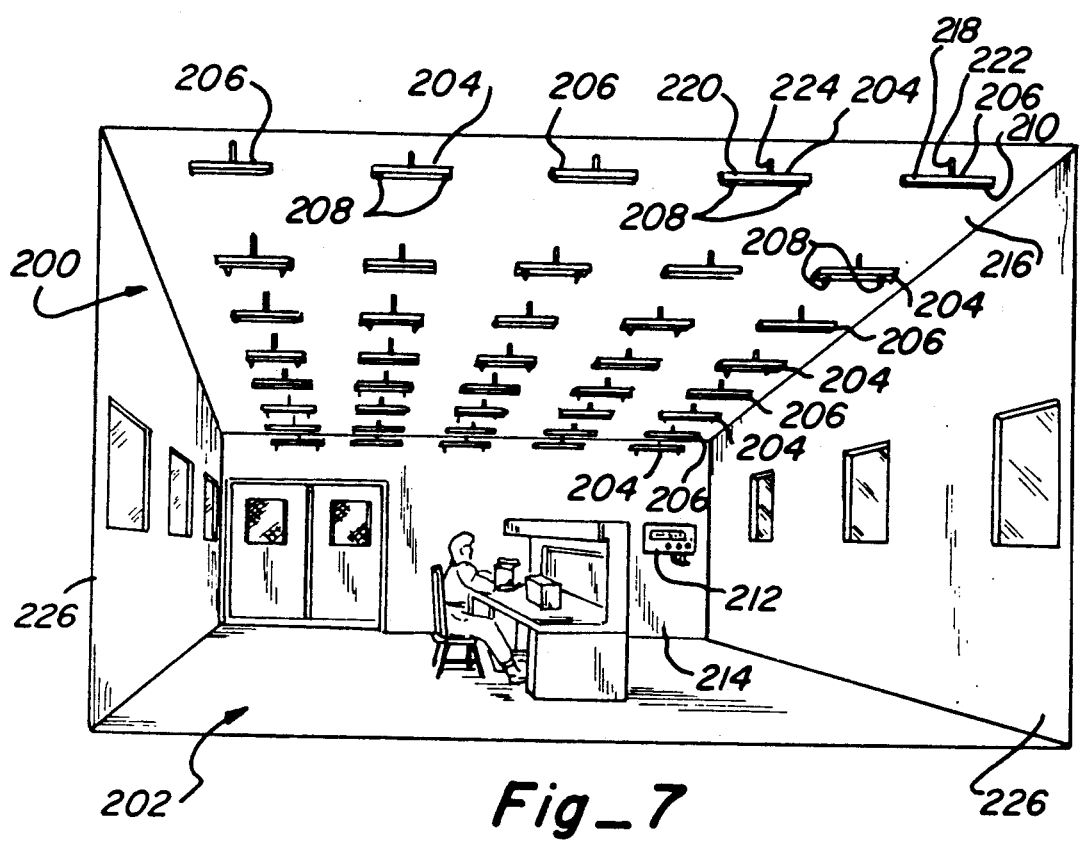
Fig_7
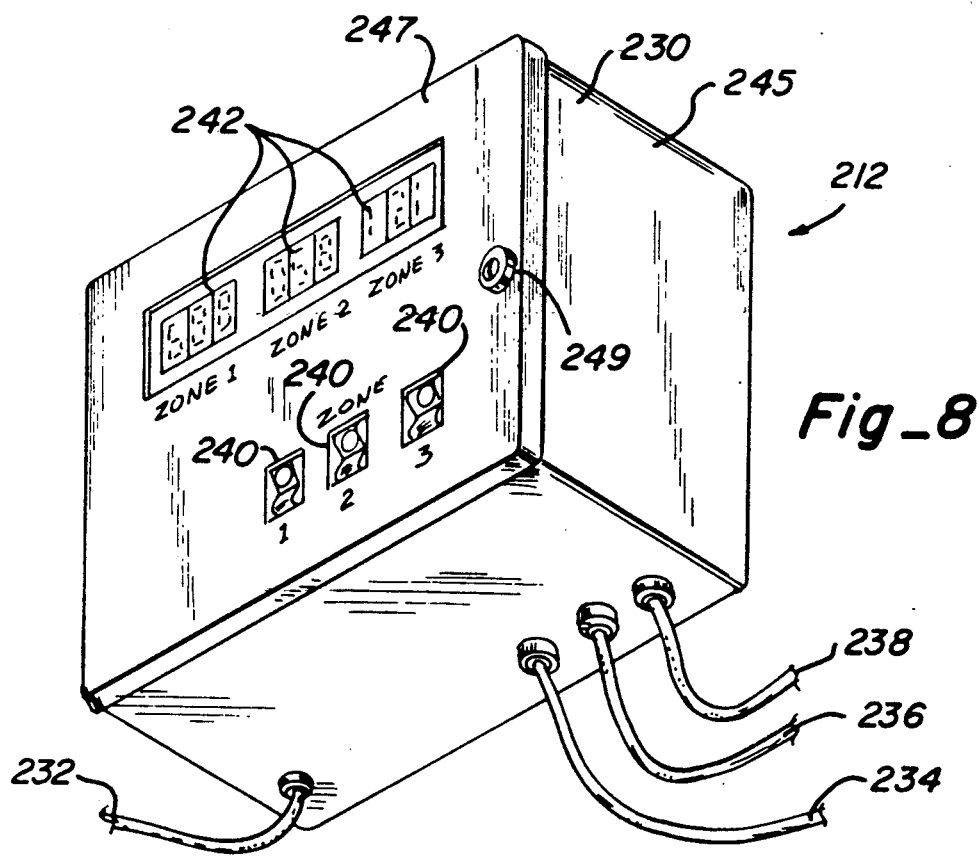
Fig_8

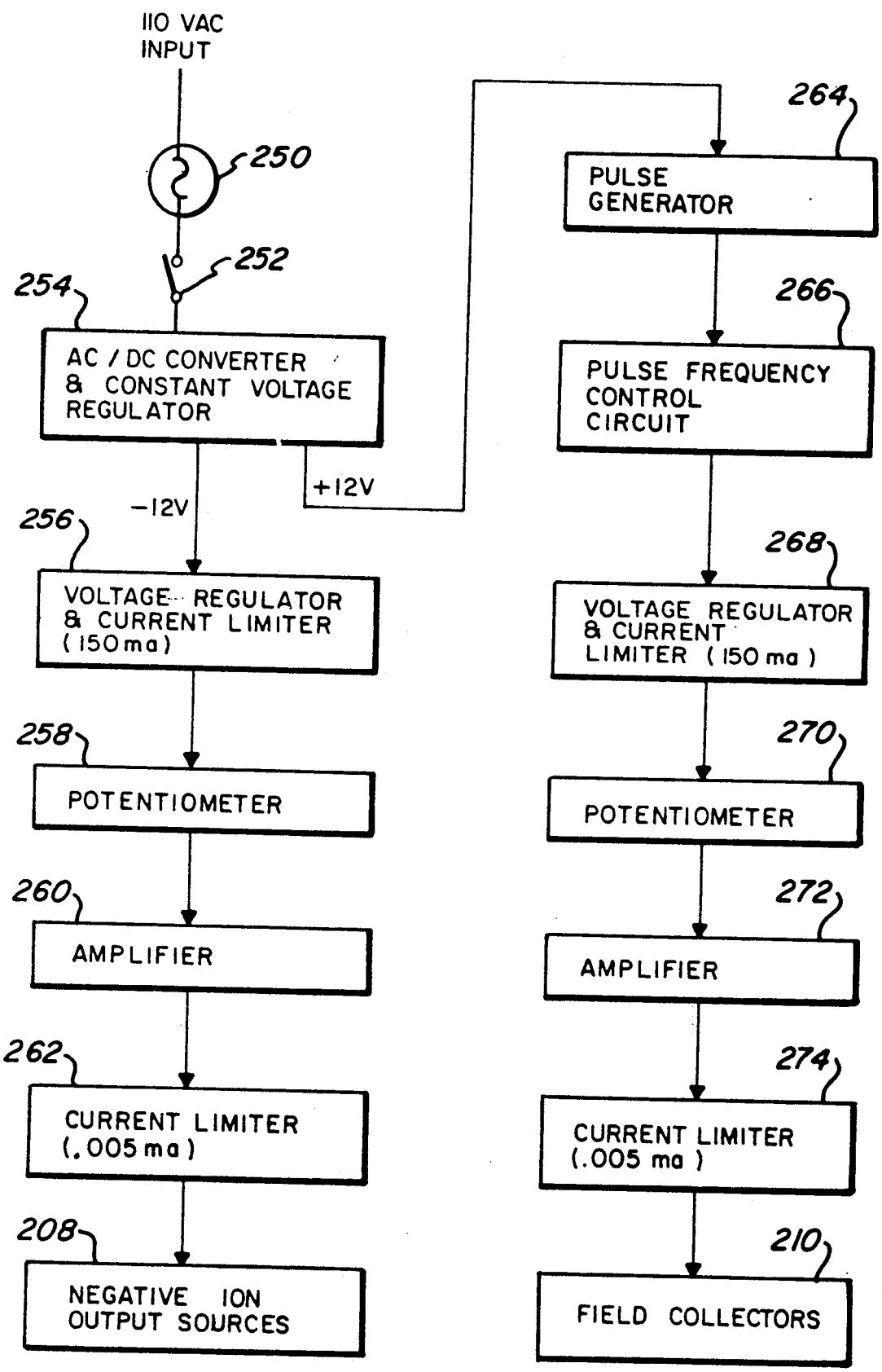
Fig_9

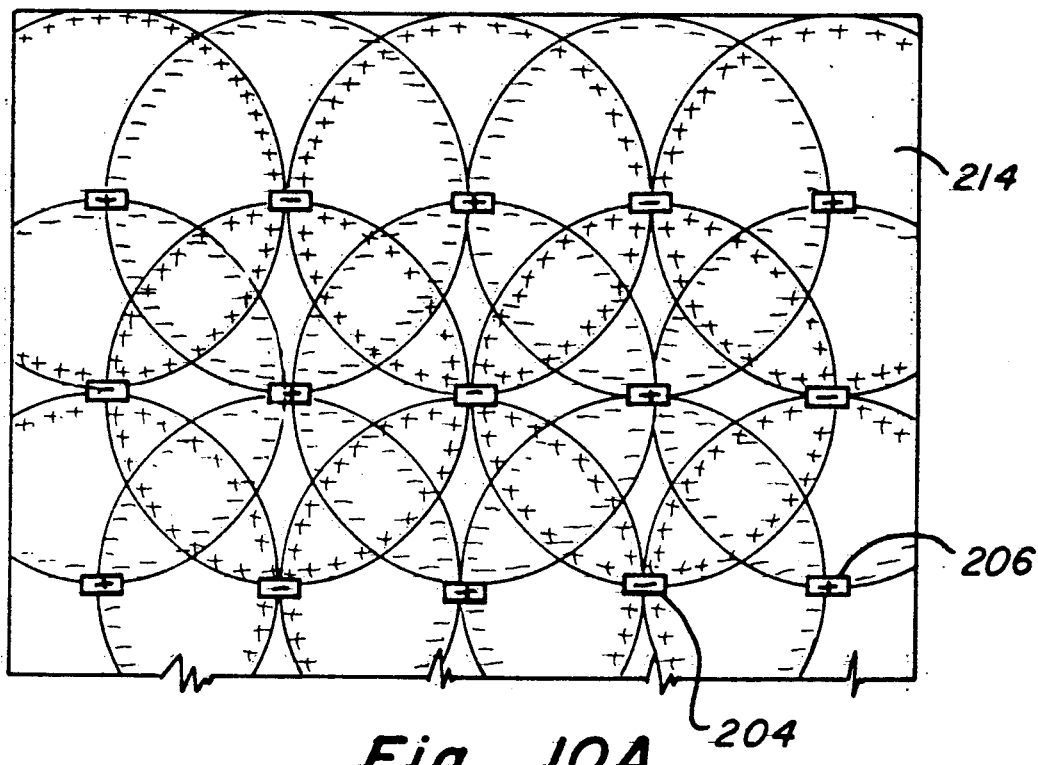
Fig_10A
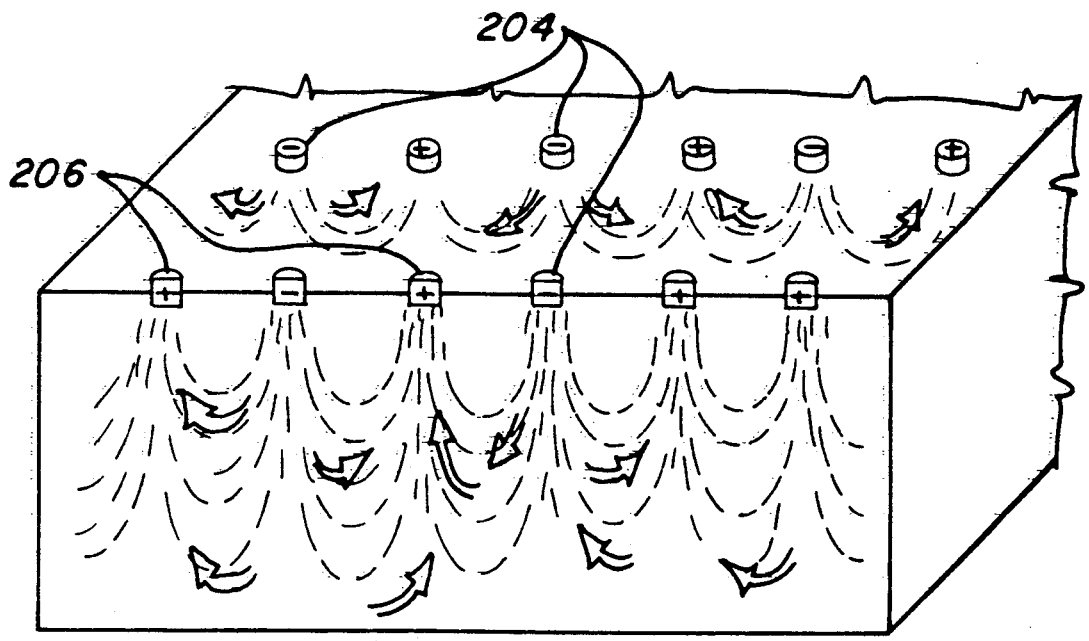
Fig_10B

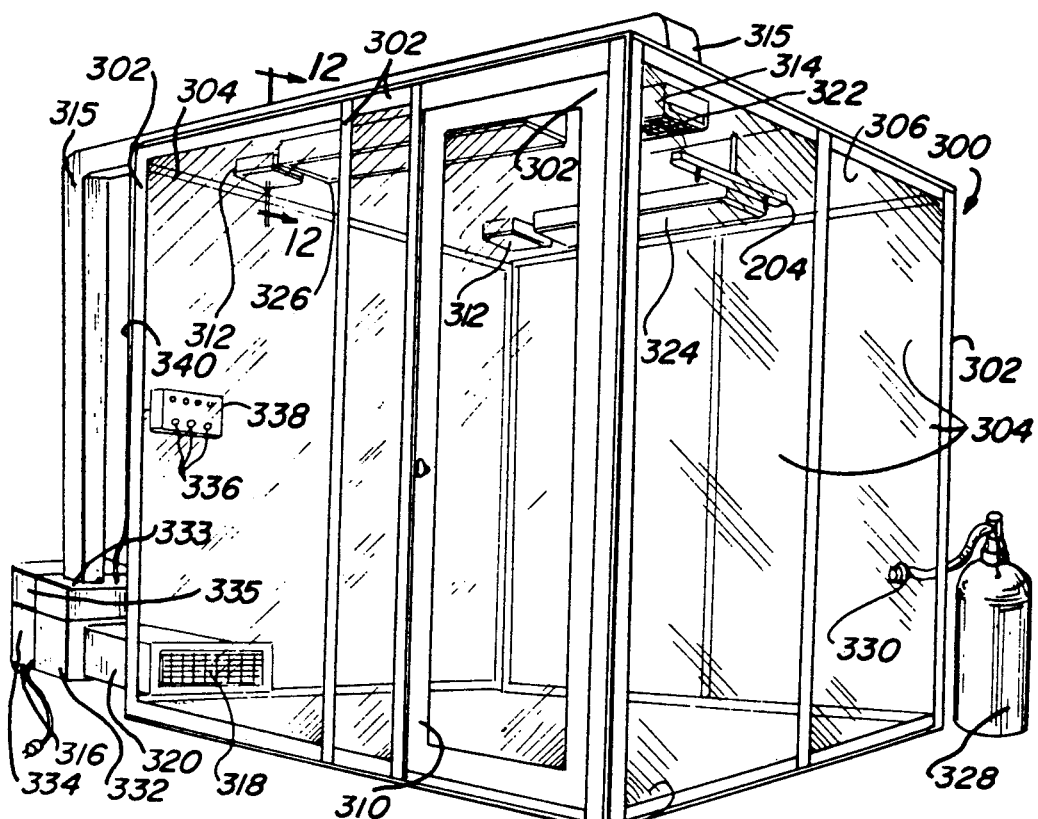
Fig_11
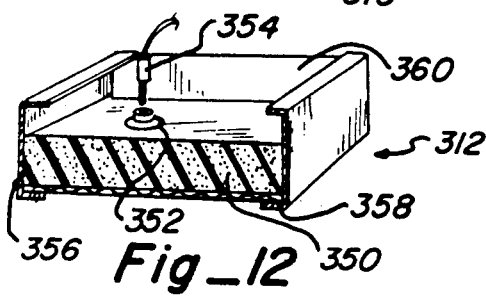
Fig_12
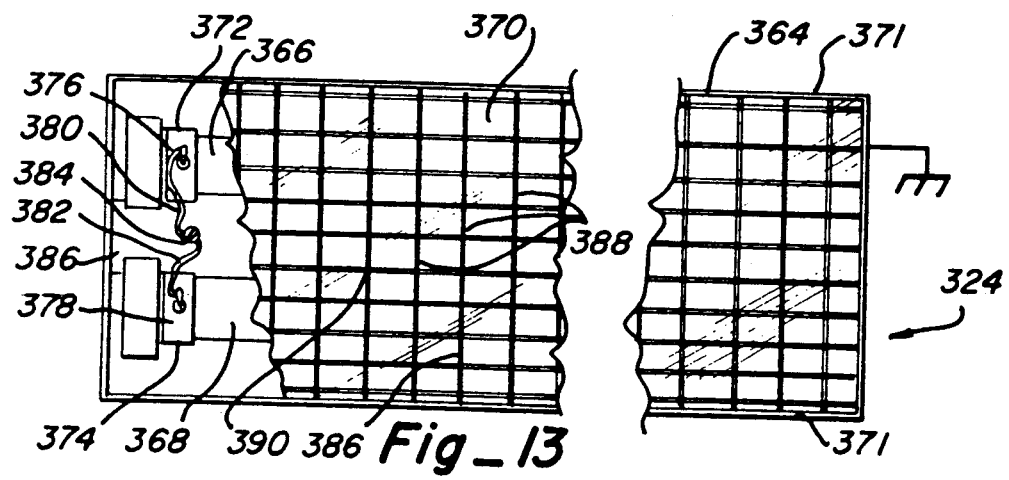
Fig_13

APPARATUS AND METHOD FOR ESTABLISHING SELECTED ENVIRONMENTAL CHARACTERISTICS

Related Applicaton

This application is a continuation-in-part of U.S. patent application Ser. No. 138,143, filed Dec. 28, 1987, and now issued as U.S. Pat. No. 4,911,737 and now pending U.S. patent application Ser. No. 300,121, filed Jan. 23, 1989.

FIELD OF THE INVENTION

This invention relates to environmental control apparatus and methods and, more particularly, relates to apparatus and methods for establishing selected environmental characteristics in an enclosed area.

BACKGROUND OF THE INVENTION

Devices for ameliorating certain adverse characteristics of interior environments and for enhancing the well being of occupants thereof are known and have heretofore included, for example, means for generating ions and for purification of air (see for example U.S. Pat. Nos. 4,542,434, 4,528,612, 4,493,247, 4,271,452, 3,662,217, 1,167,053, and Re. 27,027).

Devices are also known for provision of an electrostatic field, and/or for establishing disturbances, or pulses, in an electrostatic field within such environments (see for example U.S. Pat. Nos. 4,271,452, 3,894,852, 3,680,281, 3,678,337, 3,662,217, 3,541,390, 3,531,150, 3,483,672, 2,184,644, 1,167,053, and Re. 27,027), with one such known arrangement including provision of a plurality of units for modification of characteristics of an environment established by a cabinet, or chamber (see U.S. Pat. No. 2,184,644).

Indoor, or enclosed, environments have long been believed to shield occupants thereof from naturally occurring and beneficial electric fields which exist near the earth from 50 to 750 volts per meter, a phenomenon known as the Faraday Cage Effect, as well as shielding the occupants from the pulsed resonance within such naturally occurring fields (commonly referred to as the Schumann Resonance). Pulsating fields are believed to have positive effects on humans and have a frequency typically in a range between 7 Hz and 32 Hz (and more commonly between 7 Hz and 10 Hz) and are now also believed to accelerate particle movement within an environment. It is also believed that some such environments become ion depleted, and are, therefore, particularly susceptible to accumulation of gaseous and particulate pollutants.

It has also been suggested that provision in an enclosed environment of negative ions may stimulate biochemical reactions and/or increase the metabolic rate of those breathing the ions, and may also reduce production of the hormone serotonin that is believed to be associated with depression and fatigue. (See Yaglow, C. P., "Are Air Ions a Neglected Biological Factor?" pp 269-279, in "The Air We Breathe—A Study of Man and His Environment", Farber, S. M. and Wilson, R. H. L. Editors, Charles C. Thomas, Publisher, Springfield, Ill. (1961); Soyka, Fred, "The Ion Effect", E. E. P. Dutton Publisher (1977); Assael M., Pfeifer, Y., Sulman, F. G., "Influence of Artificial Air Ionization of the Human Electroencephalogram", Department of Applied Pharmacology, Hebrew University —Hadassah Medical School and School of Pharmacy, Jerusalem, Israel (1973); and Kreuger, A. P., Strubbe, A. E., Yost, M. G. and Reed, E. J. "Electric Fields, Small Air Ions and Biological Effects" Department of Biomedical and Environmental Health Sciences and the Naval Biosciences Laboratory, School of Public Health, Earl Warren Hall, University of California, Berkely, Calif. (1976).)

While environmental modification devices heretofore known have been provided for use in enclosed areas, such devices have not effectively provided a single installation having apparatus capable of ameliorating a plurality of adverse environmental conditions experienced in enclosed environments and/or providing a combination of enhancements to the environment, have not recognized the value of an apparatus which is selectively controllable to maximize the beneficial effects thereof, and have often been cumbersome and/or unduly complicated to install, in many cases requiring multiple installations and/or extensive modification of the interior of an area where such devices are to be utilized. As may be appreciated, therefore, further improvements could be utilized.

SUMMARY OF THE INVENTION

This invention provides an apparatus and method for establishing selected environmental characteristics in a substantially enclosed area (for example rooms, chambers and/or helmets, or head gear, worn by occupants and operators of land and sea vehicles, aircraft, spacecraft and the like), to thereby promote removal of undesired matter from the area while more nearly establishing predetermined naturally occurring environmental characteristics therein to thus enhance the utility of the area including the performance, well being and/or integrity of equipment, materials, operators and occupants of the enclosed environment.

The apparatus includes structure for establishing a substantially enclosed area having units for producing ions and establishing an electrostatic field therein, with the intensity of the electrostatic field and the quantity of ions produced being selectable independent of one another. The electrostatic field and the ions produced are opposite in polarity and the field is preferably pulsated at a selected frequency.

The electrostatic field establishing unit includes a field collector preferably having a removable collector surface constructed, for example, of electroconductive carbon foam material, glass having an electroconductive coating on one surface, electroconductive elastomers or the like. Provision of such a collector surface enables a user to remove matter collected thereat for laboratory analysis thereof to thus determine, for example, the content of undesired matter introduced into and/or produced within the enclosed area.

The apparatus may be permanently installed or be movable between different locations, and is advantageously provided with various systems for modification of interior environments including fluid directing and fluid conditioning devices providing, for example, ventilation, humidity and/or temperature controls and intake fluid filtration, for example using high efficiency particulate air (HEPA) and/or activated carbon charcoal type filters. Utilization of full spectrum illumination fixtures and/or a supplemental source of free oxygen may be desired for some installations, and occupant and/or structural grounding where desired, may be provided.

It is therefore an object of this invention to provide an improved apparatus for establishing selected environmental characteristics in a substantially enclosed areas.

It is another object of this invention to provide an improved apparatus for establishing selected environmental characteristics by providing ions and a pulsed electrostatic field within an enclosure establishing the enclosed area.

It is still another object of this invention to provide an apparatus for establishing selected environmental characteristics in an enclosure by producing negative ions and a pulsed positive electrostatic field within the enclosure, with the quantity of negative ions and the intensity of the positive electrostatic field being selectable independent of one another.

It is still another object of this invention to provide an apparatus for establishing selected environmental characteristics which provides a user with the capability of selecting a level of negative ion output, the intensity of an electrostatic field and the frequency of pulsations within the electrostatic field.

It is still another object of this invention to provide an improved apparatus for selective modification of selected characteristics of a substantially enclosed area which includes structure for establishing the substantially enclosed area, a negative ion generator for production of negative ions in the area, a positive electrostatic field collector for producing a pulsed electrostatic field thereat, fluid directing apparatus for directing fluid to and from an enclosed area and including filters for filtering the fluid directed to the area, and controls for controlling the ion generator, the pulsed electrostatic field established in the area and the fluid directing apparatus.

It is yet another object of this invention to provide an apparatus for establishing selected environmental characteristics which includes a chamber for establishing a substantially enclosed area and in which negative ions are generated and a positive, pulsed electrostatic field is established, a fluid directing and conditioning unit for directing selectively conditioned fluid to and from the chamber and including filtering means for filtering fluid directed to the chamber, and controls for independent user control of each of the quantity of ions generated, the electrostatic field intensity, the frequency of pulsations in the electrostatic field, and the fluid directing and conditioning unit.

It is another object of this invention to provide an apparatus and method for collecting and analyzing matter in a selected area wherein a selected quantity of ions and an electrostatic field are produced in a substantially enclosed area, the quantity of ions produced and the intensity of the electrostatic field being selectable independent of one another, the electrostatic field being established at a collector having a removable collector surface for collection of undesired matter within the area thereat, whereby the collector surface may be removed for removal of collected matter therefrom so that selected analysis of the matter collected from the area may be subjected to selected laboratory analysis to determine, for example, the overall content thereof.

It is yet another object of this invention to provide an apparatus for establishing selected environmental characteristics which includes a chamber having units for producing negative ions and a positive, pulsed electrostatic field therein, and which may further include apparatus for illumination of the chamber configured to inhibit introduction into the chamber of selected electromagnetic signals while substantially simulating natural sunlight therein, a source for supplementing the free oxygen content of air within the enclosed area, fluid directing and conditioning units for circulation of air in the chamber and including means for regulating the temperature and humidity of air within the chamber and/or structure for grounding the chamber and/or occupants thereof.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate complete embodiments of the invention according to the best mode so far devised for the practical application of the principles thereof, and in which:

FIG. 1A is a perspective view of a portable environmental control apparatus the control module of which is removably attachable at a preselected position in the interior of a vehicle, for example to the sun visor of an automobile, and illustrating use of the apparatus in an overall system including filtration of intake and/or recirculated air;

FIG. 1B is a front elevation view of the control module shown in FIG. 1A;

FIG. 1C is a rear elevation view of the control module shown in FIG. 1B shown in conjunction with the remotely positionable positive field collector used in the apparatus;

FIG. 2 is a block diagram of the components of a first embodiment of the portable environmental control apparatus of FIG. 1 which is operable from its own internal power source;

FIG. 3 is a block diagram of a second embodiment of the environment control apparatus of FIG. 1 operable from a 12 volt power supply system within the enclosed environment and including means for controlling the output of the apparatus;

FIG. 4A is a schematic view of the components of a third embodiment of the environmental control apparatus operable from a conventional 115 volt AC power source;

FIG. 4B is a schematic view of the pulsing unit of FIG. 4A;

FIG. 5 is a perspective view of the compact environmental control apparatus of this invention configured for use in association with a helmet worn by the operator of an aircraft;

FIG. 6 is a sectional view of the helmet portion of the apparatus of FIG. 5;

FIG. 7 is a perspective view of a fourth embodiment of this invention utilized for selectively conditioning substantially enclosed areas such as a room;

FIG. 8 is a perspective view of the control module portion of the apparatus illustrated in FIG. 7;

FIG. 9 is a block diagram of the components of the apparatus of FIGS. 7 and 8;

FIGS. 10A and 10B are schematic illustrations illustrating negative ion and positive electrostatic field distribution achieved by desired placement of the apparatus shown in FIG. 7 in a room;

FIG. 11 is a perspective view of a fifth embodiment of this invention illustrating the preferred embodiment of an apparatus utilized for substantially enclosing an area and establishing selected environmental characteristics thereat;

FIG. 12 is a sectional view taken through section lines 12—12 of FIG. 11; and

FIG. 13 is a partial elevation view particularly illustrating the illumination units of the apparatus illustrated in FIG. 11.

DESCRIPTION OF THE INVENTION

A first embodiment of the invention 15 is shown in FIGS. 1A through 1C. In FIG. 1A, apparatus 15 is shown releasably attached to sun visor 17 of automobile 19 using clip 21. Clip 21 is affixed to the housing 23 of environmental control apparatus module 25, which housing contains the electronic circuitry (preferably micro-circuits) for producing negative ions at electrodes 27 and 29 (typically needle electrodes which are conventionally mounted in housing 23) and the pulsed, positive electrostatic field emanating from field collector 31. The overall module 25 is compact, typically being, for example, approximately 4 inches long, 3½ inches wide and 1 inch thick.

Apparatus 15 is connected to the 12 volt battery of automobile 19 through the cigarette lighter housing 33 using interface 35, herein comprising lighter adapted plug 37 for linking the 12 volt supply to the circuitry of module 25 through cord 39.

Positive field collector 31, as shown in FIG. 1C, includes electroconductive carbon foam surface 45 within insulating dish housing 47, and maintained therein, for example, by nonconductive adhesive gel. Electroconductive carbon foam surface 45 may be, for example, Ensolite CEC by Uniroyal. Collector 31 is connected to module 25 by signal supply lead 49 for coupling the voltage signal from the microcircuitry of module 25 to electroconductive carbon foam surface 45 through electrode 51.

While module 25 is shown herein attached to the existing 12 volt battery of an automobile, it should be realized that the apparatus could make use of a variety of existing power sources in a variety of vehicles (for example land, marine, and air craft), and/or could make use of its own 12 volt battery pack as more fully set forth hereinbelow. In addition, while a 12 volt source is herein specified, it will be realized by those skilled in the art that the apparatus could be modified for use with power sources having different output voltages.

Housing 23 of apparatus 15 includes at the forward surface 55 thereof, on/off control 57, operational indicator lights 59 and 61 (indicator light 59 indicating that the ion generator is operational, and indicator light 61 indicating that the positive pulsed field is operational), as well as the negative ion generation electrodes 27 and 29.

By providing a module and field collector which may be selectively positionable within the particular enclosed environment, the point of generation of negative ions may be advantageously positioned to maximize intake of negative ions by a user of the device, and positioning of the positive field collector may also be advantageously selected for maximum effectiveness, for example above the head of the operator (or passenger) (using, for example, strips of the trademarked product Velcro 62 attached to dish housing 47). In addition, provisions may optionally be made for grounding of the operator and/or occupants, if desired.

If a more permanent positioning of the positive field collector 31 is desired, the field collector may be permanently installed (by use of screws, adhesives or the like) with cord 39 provided with a jack for attachment to a mating jack located in housing 23. In addition, an additional outlet receptacle 63 for provision of an additional, remote ion electrode may be provided in module housing 23. Hand-manipulable control knobs 64, 65 and 66 (as shown in FIG. 1B) may be provided at the forward surface 55 of housing 23 for adjustment of negative ion output, positive electrostatic field strength, and the frequency of pulsations provided within the field respectively (as described hereinbelow).

Air intake and/or recirculation ducts (for example duct 67) may have filters (for example filter 68) positioned therein to thereby provide filtering of particulates and gases otherwise present in the environment. The filter system is preferably a combination of a 0.3 micron high efficiency particulate air (HEPA) filter 68' and an activated carbon charcoal filter 68".

Turning now to FIG. 2, one embodiment of a circuitry for apparatus 15 is shown, with the apparatus being operable from its own 12 volt battery pack 69. The +12 DC voltage supplied from battery pack 69 is received by constant voltage regulator 70 upon activation of on/off switching mechanism 71. Constant voltage regulator 70 (for example a 12 volt Zener diode) provides a steady +12 volt signal which is received by DC step-up transformer 72, the secondary coil of which is center tapped, providing a 350 volt signal at one output and a 2,500 volt signal at the other output. The 350 volt signal is received by pulse generator 73 the output signal of which is pulsed at a frequency of about 7.830 Hz. Pulse generator 73 is connected with rectifier 74. The positive portion of the pulsed 350 volt signal is thereafter received at current limiter 75 for limiting the current of the signal to about 0.005 mA at positive field collector 31.

The 2500 volt signal from step-up transformer 72 is received at amplifier 76 where the signal is amplified providing a 3.5 KV signal which is rectified at rectifier 77. The negative portion of the signal is received at current limiter 78 (limiting signal current to 0.005 mA) and thereafter at electrodes 27 and 29 as well as auxiliary ion output interface 79.

A second embodiment of the circuitry of apparatus 15 is shown in FIG. 3 and includes interface 35 attachable to a 12 volt power source 81 already existing within the particular enclosed environment. As indicated in FIG. 3, the DC signal provided at interface 35 is coupled through switch 71 and constant voltage regulator 70 to DC step-up transformer 72 which is connected with pulse generator circuitry 73 and amplifier 76 as was previously described in FIG. 2. However, the output signals from transformer 72 are connected to potentiometers 82 and 83, potentiometer 82 allowing user regulation of the intensity of the electrostatic field produced at field collector 31, preferably within a range from 0 to 350 volts, and potentiometer 83 allowing control over voltage supplied to the negative ion output sources 27 and 29 in a range from 1.5 KV to 3.5 KV thereby allowing user regulation of the quantity of negative ions produced at the electrodes.

Pulse frequency control circuit 84 is connected between pulse generator 73 and potentiometer 83 for providing user control of the frequency of the pulses within the electrostatic field in a range from 7 to 32 Hz (preferably from 7 Hz to 12 Hz), which range corresponds with the naturally occurring pulsations in the electrostatic field surrounding the earth commonly referred to as the Schumann resonance. It is now believed that the preferable setting however will provide pulsation frequency of about 7.83 Hz.

While user controls for control of ion output, electrostatic field strength and frequency of field pulsations are shown in FIG. 3, it should be realized that control over less than all of the above parameters may be desirable in any particular embodiment of the invention, those parameters without such user control being set for a predetermined output in a desirable range as heretofore discussed.

Referring now to FIGS. 4A and 4B, the circuitry for another embodiment of the apparatus is shown for use in association with a conventional 115 volt AC power supply. The 115 volt signal is coupled through fuse 86 and switch 87 to potentiometer 88 and variable resistor 90. Potentiometer 88 is connected to step-up transformer 92 for stepping the voltage up to 1200 volts. Variable resistor 90 is connected to step-up transformer 93 for separately stepping up the voltage output from the secondary coil thereof to 1000 volts. The 115 volt signal is also provided to pulse generating circuitry 94 for providing a pulsed output having a frequency of between 7 and 12 Hz (as more fully illustrated in FIG. 4B). Indicator lamp 96 is provided for indicating operability of the apparatus upon closure of switch 87.

The output from transformer 92 is connected with amplifier and rectifier circuitry 98 for providing a rectified signal therefrom having a user controlled voltage of between 0 and −9 KV. Amplifier and rectifier circuitry 98 is a conventional circuit and includes capacitors 100, 101, 102 and 103, diodes 105, 106, 107 and 108 and resistor 110. The amplified and rectified voltage signal is supplied to negative ion output source 112 for adjustable negative ion output thereat.

The output from transformer 93 is connected to amplifier/rectifier circuitry 114, as is pulse generating circuitry 94. Amplifier and rectifier circuitry 114 includes capacitors 116 and 117 and diodes 119 and 120 in a conventional configuration, and is connected through resistor 122 to a positive field collector as previously set out herein. Variable resistor 90 enables user control over the intensity of the positive electrostatic field produced at the field collector in a range from 0 to 3.2 KV.

FIG. 4B illustrates in detail adjustable frequency pulse generating circuitry 94 overall operation of which effectively establishes a ground interrupt system for establishing and regulating pulsations in the positive electrostatic field. The 115 volt AC signal is received at step-up transformer 125 (preferably producing an output matching that of transformer 93) the opposite sides of the secondary coil of which are connected to diodes 127 and 129 for full wave rectification of the signal. The DC output from the diodes is connected to pulse producing circuit 130 which includes resistors 132 and 133 and potentiometer 135. The DC signal is received at the bases of transistors 137 and 139 through resistors 132 and 133 and diodes 141 and 143, and is received at the collectors of transistors 137 and 139 through potentiometer 135 (for control over frequency of pulsations). The emitters of transistors 137 and 139 are connected to ground. Capacitor 145 is connected between the collector of transistor 137 and the junction of the base of transistor 139 (through diode 143) and resistor 133. The out signal from circuit 130 is received at amplifier/rectifier circuitry 114 through capacitor 147.

FIGS. 5 and 6 illustrate an embodiment of apparatus 15 wherein module 25 may include circuitry substantially similar to the circuitry shown in FIGS. 2 or 3. As shown in FIG. 5, however, module 25 is used in connection with a protective head gear, for example helmet 160 (herein shown to be a helmet typical of those which may be used by aviators and the like).

As shown in FIG. 6, helmet 160 is provided with negative ion electrode 162 adjacent air intake nozzle 164, with the electrode being provided in insulating housing 166. By provision of the negative ion output at the point of attachment of nozzle 164 to mask 168, the user of helmet 160 maximizes intake of negative ions. Of course, when the apparatus of this invention is used in association with a helmet having no such air intake system and/or face mask, the position of the negative ion output electrode may still be selectively located, as set forth in FIG. 1 for example.

Signal supply line 170 is provided between electrode 162 and module 25. A second signal cord 172 from module 25 is provided at the rear of helmet 160 (and may include a jack and plug arrangement for disengagement of the line from the helmet) for connection to electrode 175 in electroconductive carbon foam surface 177. In this fashion, the positive electrostatic field is provided at the electroconductive carbon foam surface 177 within helmet 160. In other regards, the circuitry of module 25 is substantially similar to that shown in FIGS. 2 and 3, and provides for the output of negative ions and a positive electrostatic field which is pulsed within the 7 to 32 Hz range, and which may also include user controls for controlling the frequency of pulsations, the intensity of the electrostatic field, and the quantity of negative ion output.

FIG. 7 illustrates a fourth, and now preferred, embodiment of this invention utilized for selectively conditioning substantially enclosed areas such as room 202, which may be an office, clean room, or the like. Apparatus 200 includes a plurality of negative ion generators 204 and positive electrostatic field generators 206. The negative ion generators each include a pair of electrodes 208 spaced approximately 24 inches apart, and the electrostatic field generators 206 include field collector surfaces 210, for example elongate electroconductive carbon foam collector surfaces similar to those heretofore discussed.

Control unit 212 is mounted on rear wall 214 of room 202, and each of the electrostatic field generators 206 and the negative ion generators 204 are mounted to ceiling 216 utilizing housings 218 and 220, respectively, including mounting rods 222 and 224 for mounting the units adjacent to but spaced a short distance from ceiling 216.

While it is desirable to have the units mounted on the ceiling, the units could be mounted on side walls 226 or rear wall 214 (as well as a front wall, not shown herein) although it is preferable for the negative ion generators to be ceiling mounted in most cases.

It has been found that when the generators are mounted a preselected distance apart (preferably from 3 to 7 feet apart) and preferably with ion generators and electrostatic field generators being positioned alternately between side walls 226 and between rear wall 214 and the front wall, more even distribution of negative ions and the positive field is achieved providing a substantially constant voltage and polarity in the area thus minimizing charge differentials between structure (including walls, floors, equipment, work surfaces, people and the like) and undesired matter to be collected and removed from the room.

It has been found that positioning generators 204 and 206 closer than about 3 feet results in undesired field effects thereby reducing the concentration, and thus cleaning effect, of negative ions throughout an area, while a greater distance than about 7 feet between the units reduces the performance level of the apparatus by again negatively effecting the concentration and even distribution of ions in the field and thereby extending the period required for collection of undesired matter from the area (such as particulate matter, dust, processing by-products, and the like).

When installing the units in an area, a background reading of the ions and particulate matter to be removed in the 5 micron to 0.001 micron range is taken. Once the level of such particulates present in the area is known, the unit is calibrated to produce the desired concentration of negative ions and positive field strength, and the generators are installed in selected positions to achieve the desired evenness of distribution of the negative ions and positive electrostatic field within the area. For example, given a constant voltage, it is desirable for generators to be positioned more closely (for example, at 3 foot intervals) where there is a higher concentration, or more hazardous variety, of particulates to be removed, while the units would be spaced more widely (toward the 7 foot spacing) where less concentration of negative ions at some predetermined distance from the generators is desired, such as in offices and the like. Of course, concentration at given spacing within the range can be varied by adjusting the voltage at the outputs of the generators, the spacing of the generators or combination thereof.

When the apparatus is positioned as above described, a substantially constant polarity and voltage is selectively maintained within the area thus minimizing charge differentials between the various structural units in the area, equipment, people and the matter which is to be removed from the area. Particulates and other matter to be removed, having a smaller mass, will, upon exposure to the negative ions, attach to the ions within the positive field and be attracted to the positive field collectors 210 The particulates are felt to become polarized in this manner so that the negatively charged portion of the particles maintain an orientation toward the positive field collector surface, and in fact may form chain-like structures between themselves, thus further enhancing their movement toward the positive field collector.

As heretofore discussed, the positive field produced by the positive field generators is pulsed in the 7 to 10 Hz range, preferably at 7.83 Hz, with each of the pulsations having an intensity of approximately 150 to 200 volts (again simulating naturalistic ionic cavity field resonance). It is felt that the pulsations in the positive electrostatic field assist in exciting atomic and molecular motion and thus movement of the particles toward the positive electrostatic field collector surfaces 210. Furthermore, since the voltage pulsations are small relative to the overall positive voltage produced at the collector of the electrostatic field generator, substantially constant voltage is still selectively maintained in the area.

In addition, the overall beneficial effects heretofore set forth of reducing the so-called Faraday cage effect and reproducing more naturally occurring fields found within the earth's ionic cavity, thus offsetting the 50 to 60 Hz syndrome found in modern architecture, are provided, thus providing many of the same benefits to inhabitants of the area.

FIG. 8 illustrated control unit 212 including control unit housing 230, power supply cord 232, zone supply cables 234, 236 and 238, zone on/off switches 240 and zone indicators 242. The different zone switches, indicators and supply cables are provided so that ion production and electrostatic field generation can be controlled in different parts of an area while other areas are left uneffected (it being understood that only a single zone may be desirable in any given case, and that all of the zones, where multiple zones are provided, are controlled by the same internal circuitry).

Housing 230 includes wall mountable housing portion 245 and door unit 247 having a lock 249 therein for tamper free maintenance of door 247 on portion 245. While not shown herein, control unit 212 includes, within the housing, adjustment mechanisms for adjusting the quantity of negative ion output, strength of the positive electrostatic field and frequency of pulsations in the electrostatic field, as was set forth heretofore.

FIG. 9 is a block diagram illustrating the circuitry to be found within control unit 212. The unit is connected to a 110 volt AC power source and includes fuse 250 (for example a ½ amp fuse) and on/off switch 252. The 110 volt AC signal is coupled through fuse 250 and switch 252 with the input of AC to DC converter and constant voltage regulator 254, for example a POWER-ONE, Inc. HB12-1.7A AC to DC converter and constant voltage regulator unit, which provides a $-12$ volt DC and a $+12$ volt DC signal at its output.

The $-12$ volt signal output is connected to the input of voltage regulator and current regulator 256 for limiting the output signal amperage to 150 ma with an output voltage of 6 to 12 volts, depending on the particular application.

Potentiometer 258 is provided to adjust voltage to thus allow a user of the apparatus to control the quantity of ions output by the device (in a range from 500 to 5,000,000 negative ions per cubic centimeter, with the ions being in the 0.001 micron range). The signal is then amplified by amplifier 260 (for example a Murata Erie Company 7700-694-000 amplifying unit) and presented at current limiter 262 for limitation of current to .005 ma (as heretofore set forth) before coupling of the output signal to negative ion output sources, or electrodes, 208.

The $+12$ volt signal from AC to DC converter and constant voltage regulator 254 is provided at the input to pulse generator circuitry 264 which is connected to pulse frequency control circuit 266 (as previously discussed heretofore) for providing frequency controllable pulsations in the positive field. The signal from pulse frequency control circuit 266 is provided at the input of voltage regulator and current limiter 268 for regulating the voltage at 6 or 12 volts, as desired, and limiting the current to 150 ma.

The signal at the output of voltage regulator and current limiter 268 is coupled with the input of potentiometer 270 to provide user control over the intensity of the positive electrostatic field in a range between 0 and 18 kilovolts at the output of amplifier 272 (amplifier 272 being, for example, a Murata Erie 7700-327-000 amplifier). Amplifier 272 is connected to current limiter 274 for limitation of the current to 0.005 ma (current limiters 262 and 264 being substantially similar). The output signal therefrom is then coupled with field collectors 210.

FIGS. 10A and 10B are schematic illustrations of the distribution of ions within an area such as room 214, and illustrate the conical distribution of the negative ions and positive fields within the room (as shown in FIG. 10B) and the overlap of the zones of influence of the positive electrostatic fields and negative ion distribution radii to thus achieve an overall even distribution in the area of both the positive electrostatic field and negative ions.

In FIG. 11 a fifth embodiment of this invention is illustrated for use in association with enclosures. While the enclosure and related system illustrated in FIG. 11 is preferred for use with enclosures utilized for athletic training facilities, medical and dental operatories, and the like, it should be realized that fewer than all of the additional features illustrated in FIG. 11 may be utilized in any particular embodiment, for example for utilization in vacuum chambers, helmets and head gear, free standing clean room facilities, and the like.

Such an enclosure system may be used for isolation of hospital patients, for example patients suffering from asthma, cardiac conditions, stroke, or burn, medical and dental operatory rooms, clean rooms, isolated chemical laboratories, athletic training chambers, or various testing chambers wherein isolation of materials or equipment is desirable, for example for containment, collection and analysis of matter related to utilization and function of various machines, processes, materials and the like. While not specifically shown in FIG. 11, or described hereinbelow, additional known equipment could usefully be positioned in such a chamber arrangement (for example known gas analysis equipment for analyzing the makeup of gaseous fluids introduced into or produced within the chamber).

As shown in FIG. 11, chamber, or enclosure, 300 (which may be either a permanent installation or a portable installation) is provided having a plurality of structural members 302, wall members 304, ceiling members 306 and floor member 308, the chamber being made accessible to users thereof through entryway, or door 310.

Frame members 302 can be constructed, for example, of extruded anodized aluminum, with wall and ceiling members being constructed of scratch resistant, low conductivity polycarbonate material or a combination of such material and an outer glass shell, the overall construction of the chamber being configured to enclose and thus virtually isolate, or segregate, the interior area thereof from the overall environment surrounding the chamber (for example, with the wall members and frame members and door members being provided with seals to prevent leakage of contaminated air therethrough). The various structural members are joined to form chamber 300 utilizing known techniques (for example fitting of wall, ceiling and floor members into channel structures of the frame members, or utilizing known fasteners such as rivets, screws or the like).

Within chamber 300, is positioned negative ion generator 204 as heretofore described (a plurality may be used depending upon the size of the chamber) and positive electrostatic field collectors 312 (similar in many regards to field collectors 206, 175/177 and 31 heretofore described). Fluid inlet structure 314 is provided for movement of air therethrough from duct 315 (which may be rigid or flexible ducting) and fluid directing, circulating and conditioning apparatus 316 to thereby provide fresh air into the chamber. Return opening 318 is provided for return of air through duct 320 to apparatus 316 in a known fashion.

Structure 314 has provided therein filters 322 including a HEPA filter and activated carbon charcoal filters (as heretofore set forth with respect to FIG. 1A) for filtration of undesired particle matter and gaseous elements present in air supplied to the interior of the chamber. Known full spectrum UV-A.B illumination units 324 and 326 are provided, such units typically simulating up to 94% of the suns natural radiation.

A supplemental source of free oxygen is provided at oxygen supply 328 through flow control valve 330 manipulable from within the chamber to thereby allow users of the chamber to supplement the content of free oxygen within the chamber. Apparatus 316 (which may be separately provided or be part of an existing system utilized conventionally for climate control of the overall environment surrounding chamber 300), in addition to air circulation unit 332, may include a standard heating unit 333, cooling unit 334 and humidifying unit 335 therein, such units being well known in the art, with the air circulation unit, heating, cooling and humidity units being connected to sensors and level regulators 336 at control panel 338 in a conventional fashion (including temperature and humidity regulator controls and fan speed control, for example, to provide for user regulation of the temperature, relative humidity and rate of air exchange within the enclosed area of chamber 300). Control panel 338 may, in addition, include an on/off control as well as lighting controls and controls for setting the levels of the positive electrostatic field intensity, quantity of ions produced, and frequency of pulsations established within the positive electrostatic field as heretofore set forth, and is in communication with the various units controlled thereby through conduits 340.

Overall operation and function of the field collectors and negative ion generators is substantially similar to the system illustrated in FIGS. 7, 8 and 9, with positioning of the units being selected to maximize the effects thereof as heretofore set forth.

The chamber may optionally include structural grounding for grounding the structure and/or occupants and equipment within the chamber, and floor 308 may in some cases desirably be constructed of electroconductive materials. Shielded and grounded power outlets, as well as other required utilities, may be provided within the chamber.

FIG. 12 is a sectional view of one of the collectors 312 illustrating use of a removable collector surface 350 which may be constructed of electroconductive carbon foam pads (although other such removable collector surfaces could be utilized including, for example, glass having an electroconductive coated rear surface, known electroconductive plastics, or the like). Female collector plug 352 is provided for connection and disconnection to a male connector plug 354 in turn connected to a source of current for establishing the positive electrostatic field at the collector. The electroconductive carbon foam collector 350 is positioned in channel members 356 and 358 in collector housing 360 and is removable therefrom merely by lifting at one side to thus dislodge the opposing side from the channel to thereby allow disconnection of the plugs and removal of the carbon foam pad therefrom.

As heretofore set forth, in overall operation the carbon foam collector collects undesired particulate matter present in the chamber, and thus upon removal thereof from collector housing 360 may be utilized for analysis of the contaminants collected thereat. The electroconductive carbon foam pad, while being suitable for collection of such matter, is also well suited to washing, for example in deionized and distilled water or other suitable fluid, to thus remove matter collected at the collector surface. The collected contaminants and the fluid may then be centrifuged for separation of the collected matter, and analysis of the matter may then be undertaken to determine the makeup and nature thereof. Known laboratory analysis techniques, including microscopic analysis, scanning electron microscopy, spectral analysis, and resonance ionization spectroscopy, may be utilized depending on the nature of the analysis undertaken and the degree of certainty as to the relative makeup and character of the desired. Collector surface 350, may be replaced in housing 360 for further use thereof within the chamber after washing (and drying) thereof.

FIG. 13 illustrates one of the illumination units (unit 324) providing further illustration of special shielding and defusing structures utilized therewith to prevent introduction into the chamber of undesired electromagnetic signals (particularly radio frequency and x-ray radiation which may be associated with normal operation of the illumination units). While not particularly illustrated herein, transformers, ballasts, and the like associated with the illumination units have been removed from the fixture itself and positioned outside of chamber 300 adjacent to ceiling members 306.

The illumination units include housing 364 having known full spectrum UV-A.B lamps 366 and 36 connected therein in a conventional fashion. An ultraviolet transmitting defuser 370 is positioned on channel retainers 371 at housing 364 for defusing light produced at lamps 366 and 368 into chamber 300. The housing is grounded in a conventional fashion.

At cathode ends 372 and 374 of lamps 366 and 368, respectively, shields 376 and 378, respectively, surround ends 372 and 374. The shields are preferably lead shields, or alloys thereof, and may be formed into either a tape-like material or a fabricated collar configuration. The shields have ground wires 380 and 382 connected thereto for connection to ground screw 384 at rear wall 386 of housing 364 to thus shield and ground the cathode ends of the fixtures to inhibit introduction of radio frequency radiation into the chamber.

Further protection against introduction of radio frequency radiation into the chamber is provided by antenna 386 formed of a mesh of vertical and horizontal wires 388 and 390, respectively, the overall mesh being interconnected and grounded to housing 364. Antenna 386 is integrally formed in diffuser 370, but could also be a free standing antenna maintained on the rear surface thereof.

As may be appreciated from the foregoing, this invention provides an improved apparatus and method for selective environmental conditioning of substantially enclosed areas wherein an enclosure is provided having negative ions and a pulsed positive electrostatic field established therein to thereby promote removal of undesired matter, such as particulate matter, from the area while more nearly establishing predetermined natural occurring environmental characteristics therein, as well as selectively supplementing the environment thereof, to thus enhance the performance and well being of occupants and equipment therein, as well as allowing for monitoring and analysis thereof. The enclosures may be of any useful configuration and could include vacuum chambers (for example utilized for vapor deposition, plasma etching and/or sputtering processes), helmets or headgear worn by pilots or the like, isolation chambers, training chambers and/or medical and dental operatories or treatment facilities.

Conditioning of fluid (usually air) directed to the interior of the enclosure is provided, and a user of the enclosure maintains control within predetermined parameters of one or all of the quantity of negative ions generated, the intensity of, and frequency of pulsations in, the electrostatic field, the temperature and humidity of air introduced into the enclosure, the free oxygen content of air in the chamber and the rate of circulation of air through the chamber. Fluids (air) entering the enclosure are filtered to remove undesired particle and gaseous elements thereof. Specialized illumination units may be provided to simulate natural sunlight, with shields and defusers being provided to inhibit introduction into the enclosure of selected electromagnetic signals associated with normal operation of such units, and grounding systems may be provided, such as electroconductive flooring, for grounding the enclosure and/or occupants thereof.

What is claimed is:

1. A method for establishing selected environmental characteristics comprising:
   establishing a substantially enclosed area having an entry way, said enclosed area being established at least partly utilizing materials characterized by low conductivity;
   generating a selected quantity of ions within said area by applying voltage to electrode means so that ions are produced thereat;
   generating an electrostatic field within said area by applying voltage to field collector means to thereby provide a selected electrostatic field intensity within said area, said electrostatic field intensity and said quantity of ions generated being selectable independently of one another; and
   pulsating said electrostatic field at said field collector means at a selected frequency.

2. The method of claim 1 wherein said ions are negative ions and wherein said electrostatic field is a positive electrostatic field, the method further comprising collecting and analyzing matter in said selected area by providing a removable collector surface at said field collector means, generating said ions and said electrostatic field for a desired period of time sufficient to collect matter at said collector surface, removing said collector surface from said field collector means, removing said matter from said collector surface, and performing selected analysis of said matter thus removed.

3. The method of claim 2 wherein the step of removing said collected matter includes the step of washing said collector surface in distilled water to remove said collected matter therefrom and centrifuging said distilled water having said matter therein.

4. The method of claim 2 wherein the step of performing selected analysis comprises at least one of microscopic analysis, scanning electron microscopy, spectral analysis and resonance ionization spectroscopy.

5. The method of claim 2 wherein said collector surface is an electroconductive carbon foam pad, the method further comprising repositioning said collector surface at said field collector means after said collected matter is removed therefrom.

6. An apparatus for establishing selected environmental characteristics comprising:
   means for establishing a substantially enclosed area having an entry way, said means for establishing a substantially closed area being at least partly constructed of materials characterized by low conductivity;
   voltage supply means connectable with a voltage source and adapted for mounting adjacent to said means for establishing a substantially enclosed area;
   electrode means connected with said voltage supply means to generate a selected quantity of ions within said substantially enclosed area, said electrode means including housing means for mounting said electrode means within said means for establishing a substantially enclosed area;
   field collector means connected with said voltage supply means to generate a selected electrostatic field intensity within said substantially enclosed area, said electrostatic field intensity and said quantity of ions generated being selectable independently of one another, said field collector means including housing means for mounting said field collector means within said means for establishing a substantially enclosed area; and
   pulsating means for pulsating said electrostatic field at said collector means at a selected frequency.

7. The apparatus of claim 6 wherein said apparatus further comprises illumination means mounted with said means for establishing a substantially enclosed area for lighting said enclosed area, said illumination means configured to provide light which substantially simulates natural sunlight and including shielding and diffusing means to shield and diffuse selected electromagnetic signals associate with normal operation of said illumination means to thus inhibit introduction of said selected electromagnetic signals into said enclosed area.

8. The apparatus of claim 6 wherein said field collector means includes a removable collector surface for collection thereat of undesired matter in said enclosed area, said collector surface being of a material suitable to allow removal therefrom of said matter collected thereat upon removal of said collector surface from said collector means.
   air directing means operatively connected with said means for establishing said substantially enclosed area for directing air to and from said enclosed area and including filtering means for filtering air directed to said area; and
   control means connected with said voltage supply means, said electrode means, said positive electrostatic field establishing means and said air directing means for controlling said electrode means, said electrostatic field establishing means and said air directing means so that at least said electrostatic field intensity and said quantity of ions generated are selectable independently of one another.

9. The apparatus of claim 6 wherein said means for establishing a substantially enclosed area includes air intake structure and return air structure, and wherein said apparatus further comprises circulating means connected with said air intake and return air structures.

10. The apparatus of claim 9 wherein said air intake structure includes at least one of a HEPA filter and an activated carbon charcoal filter for filtering air directed to said enclosed area by said circulating means.

11. The apparatus of claim 9 further comprising conditioning means for providing selectively controlled conditioning of air directed to said enclosed area by said circulating means, said selectively controlled conditioning including at least one of controlling the temperature and controlling the humidity of air in said enclosed area.

12. The apparatus of claim 9 further comprising oxygen supply means communicating through said means for establishing a substantially enclosed area for selectively supplementing the free oxygen content of air within said enclosed area.

13. An apparatus for selective modification of selected characteristics of a substantially enclosed area comprising:
   means for establishing said substantially enclosed area having an entry way, said means for establishing a substantially closed area being at least partly constructed of materials characterized by low conductivity;
   voltage supply means connectable with a voltage source and adapted for mounting adjacent to said means for establishing a substantially enclosed area;
   electrode means mountable within said means for establishing a substantially enclosed area and connected with said voltage supply means to generate a selected quantity of negative ions within said area;
   positive electrostatic field establishing means connected with said voltage supply means for establishing a selected positive electrostatic field intensity in said area and including field collector means mounted with said means for establishing said substantially enclosed area a preselected distance from said electrode means and pulse establishing means for pulsating said positive electrostatic field at said field collector means at a selected frequency;

14. The apparatus of claim 13 wherein said means for establishing said substantially enclosed area is a chamber at least partly constructed of polycarbonate materials characterized by low conductivity.

15. The apparatus of claim 14 wherein said chamber includes grounding means for grounding said chamber and occupants thereof.

16. The apparatus of claim 15 wherein said chamber includes an electroconductive floor.

17. The apparatus of claim 13 further comprising temperature and humidity regulating means connected with said air directing means for regulating the temperature and humidity of air directed to said enclosed area, and wherein said control means includes level adjusting means for user control over temperature and humidity levels and the exchange rate of air in said enclosed area.

18. The apparatus of claim 17 further comprising illumination means mounted in said substantially enclosed area for lighting said enclosed area and configured to inhibit introduction into said enclosed area of selected electromagnetic signals while substantially simulating natural sunlight therein.

19. An apparatus which is movable between selected locations for establishing selected environmental characteristics comprising:
   a chamber for establishing a substantially enclosed area;
   voltage supply means connectable with a voltage source and adapted for mounting adjacent to said chamber;

electrode means connected with said voltage supply means to generate a selected quantity of negative ions in said area;

positive electrostatic field establishing means connected with said voltage supply means for establishing a selected positive electrostatic field intensity in said area and including field collector means mounted in said area and pulse establishing means for pulsating said positive electrostatic field at said field collector means at a selected pulsation frequency;

air directing and conditioning means operatively connected with said chamber for directing selectively conditioned air to and from said substantially enclosed area and including filtering means for filtering air directed to said area; and control means connected with said voltage supply means, said electrode means, said electrostatic field establishing means and said air directing and conditioning means for selecting said quantity of ions generated, said electrostatic field intensity, said pulsation frequency and air directing and conditioning characteristics independently of one another.

20. The apparatus of claim 19 wherein said field collector means of said positive electrostatic field establishing means includes a removable electroconductive carbon foam collector pad.

21. The apparatus of claim 19 wherein said chamber is constructed of materials characterized by low conductivity.

22. The apparatus of claim 21 wherein said fluid directing and conditioning means includes temperature and humidity regulating means and wherein said control means provides for user control of temperature and humidity levels in said enclosed area.

23. The apparatus of claim 22 wherein said control means provides user control of said quantity of ions generated in a range of from about five hundred to five million ions per cubic centimeter, of said electrostatic field intensity in a range from about zero to +10 KV and of said pulsation frequency in a range from about 7 to 10 Hz.

24. The apparatus of claim 22 further comprising full spectrum lighting means mounted with said chamber for lighting said enclosed area and including shielding means and diffusing means together substantially preventing introduction of radio frequency signals associated with normal operation of said lighting means into said enclosed area.

25. The apparatus of claim 24 further comprising oxygen supply means operatively connected to said chamber for selective supplementing the free oxygen content of fluid in said enclosed area.

* * * * *